United States Patent [19]

Yu

[11] Patent Number: 4,680,358

[45] Date of Patent: Jul. 14, 1987

[54] STYRYL TERMINATED MACROMOLECULAR MONOMERS OF POLYETHERS

[75] Inventor: Simon H. Yu, North Ridgeville, Ohio

[73] Assignee: The B F Goodrich Company, Akron, Ohio

[21] Appl. No.: 796,364

[22] Filed: Nov. 8, 1985

[51] Int. Cl.[4] ............... C07C 41/03; C07C 43/23; C07C 43/178; C08F 220/20; C08F 116/16

[52] U.S. Cl. .............. 526/292.9; 525/328.9; 525/379; 526/320; 526/329.6; 526/333; 526/334; 528/29; 528/103; 528/110; 568/607; 568/608

[58] Field of Search ............. 568/607, 608; 526/333, 526/334, 320, 292.9; 528/29, 103, 104, 110, 205, 393; 525/328.8, 342, 379

[56] References Cited

U.S. PATENT DOCUMENTS

| | | |
|---|---|---|
| Re. 31,468 | 12/1983 | Hsu ................. 528/408 |
| Re. 31,469 | 12/1983 | Riew ................ 528/408 |
| 3,100,804 | 8/1963 | Abramo ............. 568/607 |
| 3,190,925 | 6/1965 | Stowe .............. 526/333 |
| 3,305,565 | 2/1967 | Mueller ............. 528/408 |
| 3,627,022 | 12/1971 | Shields ............. 164/23 |
| 3,627,822 | 12/1971 | Sundby .............. 568/62 |
| 3,651,152 | 3/1972 | Umbach et al. ...... 568/607 |
| 3,794,608 | 2/1974 | Evani et al. ....... 568/607 |
| 3,850,856 | 11/1974 | Dreyfuss ........... 528/408 |
| 3,875,202 | 4/1975 | Steckler ........... 568/607 |
| 3,910,878 | 10/1975 | McAda .............. 568/608 |
| 3,963,684 | 6/1976 | Evani et al. ....... 568/607 |
| 4,140,667 | 2/1979 | Preston et al. ..... 526/333 |
| 4,186,271 | 1/1980 | Preston et al. ..... 568/607 |
| 4,327,201 | 4/1982 | Kennedy et al. ..... 525/319 |
| 4,359,589 | 11/1982 | Brownscombe ........ 568/607 |
| 4,431,845 | 2/1984 | Young et al. ....... 568/606 |
| 4,451,618 | 5/1984 | Okamoto ............ 525/349 |
| 4,485,211 | 11/1984 | Okamoto et al. ...... 525/56 |
| 4,543,397 | 9/1985 | Woods et al. ....... 528/110 |
| 4,640,849 | 2/1987 | Woods et al. ....... 528/110 |

FOREIGN PATENT DOCUMENTS

53-79833 7/1978 Japan .

*Primary Examiner*—Veronica P. Hoke
*Attorney, Agent, or Firm*—Alfred D. Lobo; Alan A. Csontos; Gregory N. Clements

[57] ABSTRACT

A cationic ring-opening polymerization of a cyclic ether ("CE") in conjunction with an unsaturated alcohol (propagator) having a styryl or substituted styryl group, produces a polyether macromer having the styryl group near one end and a hydroxyl group at the other. The polymerization proceeds by polyaddition of the CE to the OH group which is the propagating species. The CE is an alkylene oxide or an aliphatic or aromatic glycidyl ether; the propagator is a primary or secondary alcohol. The catalyst is a Friedel-Crafts acid, strong protic organic or inorganic acid, oxonium salt, or the like. Plural cyclic ethers may be (a) sequentially polymerized to form macromer block copolyethers, or, (b) polymerized randomly to form macromer copolyether copolymers. The cationically ring-opened macromer formed always contains a trace of a cyclic oligomer of the CE. The macromer formed may be homopolymerized to yield a homopolymer of the macromer with pendant chains of polymerized CE; or the macromer may be copolymerized with a wide variety of olefinically unsaturated monomers to form a copolymer of macromer.

14 Claims, No Drawings

STYRYL TERMINATED MACROMOLECULAR MONOMERS OF POLYETHERS

BACKGROUND OF THE INVENTION

This invention relates to macromolecular monomers ("macromers" for brevity) of polyethers having a styryl functional "head" group at one end, and a terminal hydroxyl (OH) group at the other end. The macromer is polymerizable through the head group with a copolymerizable monomer, and a terminal hydroxyl (OH) group at the other end. The polymerization of the macromer generates a polymacromer with a saturated hydrocarbon backbone having polyether branches thus resulting in a graft or comb copolymer. Such polymerization of the macromer of this invention, to form comb copolymers, differs from graft copolymerization in the sequence of formation of the backbone relative to the formation of the graft unit.

The macromer is formed by cationic ring-opening polymerization of a cyclic ether ("CE") in conjunction with an alkenyl alcohol, more specifically a styryl or substituted styryl alcohol ("S/subsS" for brevity), which functions as the generator of the propagating species, and a suitable cationic ring-opening catalyst. The S/subsS alcohol (referred to as the "propagator" because it functions as the propagating species (OH group) generator in the presence of a cationic initiator) if substituted, has substituents which do not interfere with the initiation, propagation and transfer reactions which generate the macromer in a polymerization which has the characteristics of a living polymerization.

It should be recognized that obtaining a S/subsS alcohol is a challenging task, per se. The simplest way to do so is to hydrolyze chloromethylstyrene ("ClMS") in the presence of an inhibitor. However, despite a large excess of inhibitor, most of the S/subsS obtained and much of the ClMS are both polymerized. Thus, it is immediately evident to one contemplating the use of S/subsS as the essential reactant for the macromer, that it is not likely that the monomeric S/subsS will survive long enough to serve its proposed function in the formation of the macromer.

It is to be noted that the macromers of this invention are formed by cationic ring-opening and not carbocationic polymerization, though both are classified as cationic polymerizations and often use the same cationic initiator. The cationic ring-opening involves the opening of strained rings of cyclic monomers and the propagating species is an oxonium, sulfonium or ammonium ion; carbocationic polymerization involves substituted olefinic monomers where the propagating species is a carbenium ion.

Numerous macromers of polytetrahydrofuran (polyTHF) have been synthesized by "living" cationic ring-opening polymerization involving an acrylic end group, inter alia, all by end-capping. But acrylic double bonds are quite different from styryl double bonds, and acrylic monomers are not cationically polymerizable (see *Principles of Polymerization* by G. Odian, Chap. 3, Table 3.1, McGraw Hill, New York 1970). Thus, hydroxyalkyl acrylates and methacrylates are unique chain transfer agents which are not cationically polymerizable (see U.S. Pat. No. Re. 31,468). On the other hand, the double bond of a styryl monomer is polymerizable with a cationic, anionic, or free radical initiator. There was no reason to expect that a monohydroxyl-terminated S/subsS propagator would remain intact under the conditions suitable for a cationic ring-opening polymerization.

To avoid the side reactions which interfere with the use of olefinic monomers, U.S. Pat. No. 4,327,201 to Kennedy and Fritsch teaches the formation of a poly(isobutylene) macromer with the use of vinyl benzyl halide and an allylic halide in conjunction with a variety of Lewis acid catalysts suited for carbocationic polymerization. In a later publication, Kennedy & Lo indicate concern over loss of a head group during synthesis, and found a specific catalyst which would avoid such loss. (see "Macromers by Carbocationic Polymerization II. An Improved Synthesis of Polyisobutenylstyrene and its Copolymerization with Methyl Methacrylate and Styrene" *Polym. Reprint* 23, pg. 99, No. 2 Sept. '82).

Much effort has been directed to the preparation of various OH-terminated difunctional and polyfunctional polyethers by cationic ring-opening polymerization of a CE in conjunction with water or an alcohol or a diol or a polyol as disclosed in U.S. Pat. Nos. 3,129,232; 3,305,565; 3,850,856; 4,284,826; 4,077,991; 3,419,532; 3,402,169; 3,269,961; inter alia.

U.K. Patent Appln. No. 2,021,606A and U.S. Pat. No. 4,431,845 teach that OH-terminated poly(chloroalkylene ethers) have not proven entirely satisfactory when prepared by cationic ring-opening polymerization as disclosed in U.S. Pat. Nos. 3,850,856; 3,910,878; 3,910,879; and, 3,980,579. Thus, the problems inherent in the use of prior art catalysts referred to in the foregoing U.S. patents have been documented. A solution to the problems was provided in the aforementioned U.S. Pat. No. 4,431,845. This solution was to use a catalyst comprising (i) a fluorinated acid catalyst having the formula $H_mXF_{n+m}$ wherein X is selected from boron, phosphorus, arsenic and antimony, m is 0 or 1, and n is 3 when X is boron and n is 5 when X is phosphorus, arsenic and antimony, and, (ii) a polyvalent tin compound.

This patent reference teaches that only tin fluorometallic compounds even among other Group IV metals, has a peculiar catalytic action not attributable to Group V fluorometallic compounds. With this catalyst, it is suggested that any aliphatic OH-containing material such as a monomeric or polymeric mono- or polyhydric alkanol, haloalkanol or polymeric glycol having up to 6 OH groups, whether terminal or pendant, may be used in the formation of a polymer with an alkylene oxide, provided at least about 50% by weight (wt) of the alkylene oxide is a chloroalkylene oxide.

The reaction of a CE with an ethylenically unsaturated alcohol in the presence of a cationic catalyst is disclosed in U.S. Pat. Nos. 3,627,822 and 3,419,621 to yield a monoadduct, the addition of a single cyclic ether (oxirane) unit to the alcohol.

U.S. Pat. No. 4,485,211 to Okamoto discloses the use of a hydroxyl-containing material (HCM) having a single OH propagating site to form block copolymers of polyethers. The HCM may be an alkylene glycol such as ethylene glycol, or a prepolymer with plural OH propagating sites, such as poly(glycidyl ether) with 2 sites. U.S. Pat. No. 4,451,618 to Okamoto discloses the use of a hydroxyl-terminated prepolymer (HTP) with one or more OH end groups which also yield polyether block copolymers. With the emphasis on the essentiality of the OH propagating sites and the routine use of saturated end groups, the possibility that a vinyl group, and more specifically, a styryl end group might survive the conditions of cationic ring-opening polymerization simply escaped notice. In view of the large number of olefinically unsaturated monomers which undergo polymerization (see the list in *Carbocationic Polymerization* by Kennedy, J. P. and Marechal, E., Table 3.6, pp 37 et seq., John Wiley & Sons 1982) the fate of the double bond of the propagator seemed speculative.

SUMMARY OF THE INVENTION

It has unexpectedly been found that, under particular conditions, a cationic ring-opening polymerization of a cyclic ether ("CE") in conjunction with an ethylenically, more particularly a styryl or substituted styryl ("S/subsS") referred to herein as a "styrylically unsaturated" alcohol, and a cationic ring-opening catalyst, produces a polyether macromer having a styryl group near one end and a hydroxyl (OH) group at the other. The styryl group of the alcohol does not undergo carbocationic polymerization under the acidic conditions required for the cationic ring-opening polymerization of the CE used. The polymerization proceeds by polyaddition of the CE to the OH group which is the propagating species.

It is therefore a general object of this invention to provide a process for the manufacture of a polyether macromer having a styryl group near one end and a hydroxyl group at the other, comprising, polymerizing (A) a cationically ring-openable cyclic ether selected from the group consisting of (i) at least one alkylene oxide having the structure

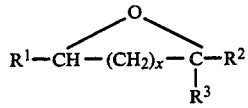
(I)

wherein, x is an integer in the range from 0 to about 4, except that when x>1, a second alkylene oxide having x=1 or 0 must be present, and, $R^1$, $R^2$ and $R^3$ are independently selected from the group consisting of hydrogen, $C_1$-$C_{20}$ alkyl (having from 1 to about 20 carbon atoms) and haloalkyl, and, $C_6$-$C_{20}$ aryl and aralkyl, and, at least one of $R^1$, $R^2$, and $R^3$ is hydrogen; and, (ii) an aliphatic or aromatic glycidyl ether having the structure

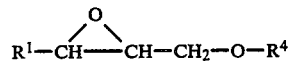
(II)

wherein $R^1$ has the same connotation as hereinabove; and, $R^4$ represents a member selected from the group consisting of a substituted group such as a hydrocarbon group, i.e. $C_1$-$C_{20}$ alkyl or substituted alkyl, particularly haloalkyl, alkoxyalkyl, aryl (Ar) or substituted aryl (Ar-Q), particularly wherein Q represents $C_1$-$C_{10}$ alkyl, or haloalkyl; and, (B) a monoolefinically ("styrylically") unsaturated primary or secondary alcohol represented by the structure

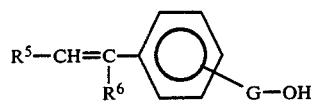
(III)

wherein,

G, if present, is an ortho-, meta-, or paraposition of the phenyl ring which may be substituted, said position being relative to that of the olefinically unsaturated group, and is a spacer selected from the group consisting of branched or linear alkyl, aralkyl, haloalkyl, haloaralkyl, alkoxyl, haloalkoxyl, aralkoxyl and haloaralkoxyl, each having from 1 to about 20 carbon atoms ($C_1$-$C_{20}$); and, $R^5$ and $R^6$ are selected from the group consisting of hydrogen, $C_1$-$C_{10}$ alkyl (having from 1 to about 20 carbon atoms) and haloalkyl, and, at least one of $R^5$ and $R^6$ is always H;

in the presence of an effective amount of (C) a cationic initiator selected from the group consisting of Friedel-Crafts acids, relatively strong protic organic and inorganic acids, oxonium salts and stable carbenium ions;

so as to produce a macromer having the structure

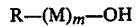
(IV)

wherein

R represents the residue of said styrylically unsaturated alcohol,

M represents the residue of at least one said cyclic ether which is ring-opened, and, m represents an integer in the range from 2 to about 500, more preferably from 2 to about 100.

It has further been found that a macromer block copolyether may be prepared by polymerizing plural cyclic ethers sequentially, or by using a macromer of this invention as a propagator, so as to have the structure

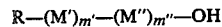
(V)

wherein

M' and M" represent two ring-opened cyclic ethers, and, m' and m" are integers each in the range from 1 to about 300 such that $m'+m''=m$.

It has also been found that a random copolymer of macromer may be prepared by polymerizing a polyether macromer IV or V with an olefinically unsaturated monomer so as to have the structures

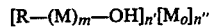
(VIa)

and,

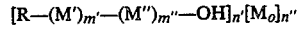
(VIb)

wherein $M_o$ represents the olefinically saturated monomer;

n' represents an integer in the range from 1 to about $10^4$, preferably 1-$10^3$ and refers to the number of pendant OH-terminated polyether chains;

n" represents an integer in the range from 1 to about $10^5$, more preferably 1-$10^4$; and, R, M, M', M", m, m' and m" have the same connotation as before.

It is a specific object of this invention to provide an essentially linear polyether macromer having styrylic and OH chain ends, and substantially uniform molecular weight distribution such that its ratio of Mw/Mn is not above about 5.0, and preferably less than 2.0.

It is another specific object of this invention to provide polyurethanes by cross-linking of the terminal OH groups on pendant polyether chains with polyisocyanate; such pendant chains are present when IV or V are polymerized to yield a polymer (VIa, b).

Still other specific objects of this invention are to provide (a) a poly(haloepoxide) macromer which may be quaternized to yield antistats, fiber softeners, excipients for drugs and biomimetic agents; and, (b) poly(siloxane-ether) block copolymer surfactants and foam stabilizers.

DETAILED DESCRIPTION OF PREFERRED EMBODIMENTS

The cationic ring-opening polymerization disclosed herein occurs because of the specific acid catalysts used with the styrylically unsaturated alcohol used to function as a chain propagator for the ring-openable cyclic ether ("CE"). This reaction was not expected to produce the macromer of this invention because it was not realized that the styryl group of the alcohol would neither polymerize prematurely nor interfere with the CE to be ring-opened by the catalyst. Macromers of this invention have a Mn in the range from about 200 to about 3000 though even higher mol wts up to about 10,000 may be formed, if desired. The term "macromer" is used herein to denote at least one of the above-specified ring-opened CE with an "S/subsS", that is, styrylically unsaturated as defined, head group. If the macromer is formed from a single CE it is referred to as a "homomacromer"; if from more than one comonomer which appears randomly, it is referred to as a "macromer copolymer"; and, if a copolymer is specifically formed by sequential copolymerization, it is referred to as a "macromer block copolyether".

To facilitate this ring-opening polymerization with living characteristics so that the styrylic head group survives the reaction without forming an excessive amount of cyclic oligomers and other undesired by-products so as to make the reaction uneconomical, it is essential that one use (i) a catalytic amount of a catalyst (initiator) which, though not narrowly critical, is preferably boron trifluoride ($BF_3$) or tin tetrachloride ($SnCl_4$); or borontrifluoride etherate complexes; or, a fluorinated metallic acid catalyst having the formula $HMF_6$ wherein M is selected from P, As or Sb; or, an oxonium salt of the acid; or, oxonium salts of tetrafluoroboron; and, (ii) an "S/subsS" alcohol with structure (III) which is at least partially soluble, and more preferably, is completely soluble in the reaction mass, with or without a solvent.

If the CE and the alcohol are not mutually soluble, or soluble in a mutual co-solvent, the polymerization will not proceed satisfactorily. The higher the solubility, generally the better the polymerization reaction. The reaction is most preferably carried out in a bulk polymerization in a simple and convenient manner.

Typically, the CE (I) or (II) and the alcohol (III), each of which is moisture-free, are charged to a jacketed glass-lined reactor provided with a mechanical agitator and fitted with a thermoprobe and condenser. The reactor is purged with nitrogen and warmed to the polymerization temperature. The catalyst, for example, triethyloxonium hexafluorophosphate (TEOP) dissolved in methylene chloride is dripped in and the temperature of the reaction mass is controlled to provide a satisfactory rate of polymerization by raising or lowering the temperature of the circulating medium in the jacket.

The polymerization is generally carried out at a temperature in the range from about 25°–50° C. but this range is not critical, some polymerizations proceeding satisfactorily at as low as 0° C., or lower, and others at as high as 90° C., or higher. The progress of the reaction is monitored by measuring total solids. Upon completion, the polymerization is terminated with aqueous sodium bicarbonate solution, and an antioxidant such as Goodrite ®3114 is added, and the temperature of the mixture raised to about 60° C. and maintained for about an hour. The liquid macromer is separated from the aqueous phase and washed with distilled water at room temperature. Unreacted monomer, if any, may be removed by distillation under vacuum in the presence of an adequate amount of a suitable free radical pollymerization inhibitor such as monomethyl ether of hydroquinone (MEHQ).

The conversion to the macromer and its mol wt are controlled by the ratio of the monomer to the alcohol, according to the following equation:

$$Mn = \left[\frac{Monomer, g}{Alcohol, g} + 1\right] \times$$

mol wt of alcohol × % total solids

About 0.1–0.5 g of TEOP is used per kg of monomer. The amount of sodium bicarbonate used as a short-stop is about three times the amount of TEOP. The amount of antioxidant added is about 0.2% by wt of the macromer. It is essential that all reactants be moisture-free because each molecule of water, if present, will initiate a polymer terminated with OH groups at both ends of the chain.

The macromer is characterized by gel permeation chromatography (GPC) analysis at 40° C. using a Water's 200 with columns packed with Styragel. THF is used as carrier solvent. All mol wts are calibrated relative to polystyrene. Cyclic oligomers, if present, and they usually are in a small amount in the range from a trace, that is about 10 ppm to about 10% by wt or more, are excluded from the calculation of mol wts. Relatively low molecular weight (mol wt) macromers, particularly those having from 2 to about 20 repeating units, are formed with substantially uniform mol wt distribution such that the ratio of the weight average mol wt (Mw) to the number average mol wt (Mn) is not substantially above about 5, preferably less than 2.

The presence of cyclic oligomers provides a "fingerprint" of a macromer formed by cationic ring-opening; a macromer of identical structure, if prepared by anionic polymerization will be free of cyclic oligomers. Examples of macromers of polyethers prepared by anionic polymerizations are found in Japan No. 70 28,786 (Chem. Absts. 74, 14138r (1971); Japan No. 74, 15,480; and U.S. Pat. No. 3,875,202.

FT infrared spectra were recorded with a Nicolet 7199 spectrometer. Samples were prepared by applying a thin coat of macromer on a KBr crystal.

Carbon-13 NMR spectra were obtained at 20.1 MHz using a Bruker WP-80 spectrometer. Macromers were examined as a 20 wt % solution in benzene-$d_6$ or chloroform-d with internal tetramethylsilane reference at 30° C.

Proton NMR spectra were obtained at 200.13 MHz in chloroform-d at 30° C. using a Bruker WH-200 spectrometer. Trichloroacetylisocyanate was used as a derivatizing agent for the OH group analysis.

Mass spectra were obtained with a Varian MAT 311A mass spectrometer in the field desorption mode. Samples were dissolved in either methanol or THF. The solution was then saturated with solid LiBr so that the lithiated molecular ions [MLi]$^+$ were produced during analysis.

Glass transition temperature ($T_g$) is determined by a Perkin-Elmer DSC-2 differential scanning calorimeter at a 40° C./min heating rate under helium.

Hydroxyl number (OH No.) was determined by acetylation with an acetyl anhydride-pyridine mixture according to a standard procedure and the end point is determined by automatic titration. The OH No. is defined as the milligram equivalent of KOH per gram of the macromer, where a mole of KOH is equivalent to one mole of OH group.

The halogen, for example, chlorine content is measured by a modified Shoniger method and used to calculate the number of epichlorohydrin ("ECH") units in the macromer.

Among the alkylene oxides having structure (I) which may be used are (i) 1,2-epoxides such as ethylene oxide, propylene oxide, cis- and trans- but preferably cis-butene-2-oxide, cis- and trans-pentene-2-oxide, cis- and trans-hexene-2-oxide, cis- and trans-hexene-3-oxide, and the like;

(ii) 1,3-epoxides such as oxetane and its derivatives; and, (iii) haloalkyl epoxides (epihalohydrins) such as 1-chloro-2,3,epoxypropane (ECH), 1-bromo-2,3-expoxypropane (epibromodydrin), 1-chloro-2,3-epoxybutane, 1-iodo-2,3-epoxyhexane, 3-chloro-4,5-epoxyoctane, 1-chloro-2,3-epoxycyclohexane, 1-bromo-2,3-epoxymethylbutane, 2-chloro-2-methyl-3,4-epoxypentane, and the like; and, (iv) 1,4-epoxides such as tetrahydrofuran ("THF"), 1,5-epoxides such as tetrahydropyran ("THP"), and 1,6-epoxides such as oxepane ("OXP") do not form homomacromers with styryl head groups. THP does not even form copolymers with 1,2- or 1,3-epoxides, but THF and OXP do. The copolymers of THF or OXP with 1,2- or 1,3-epoxides are random.

Among the aliphatic or aromatic glycidyl ethers having structure (II) which may be used, are methyl glycidyl ether, ethyl glycidyl ether, methylethyl glycidyl ether, butyl glycidyl ether, 2-ethylhexyl glycidyl ether, phenyl glycidyl ether and the like.

Among the monoolefinically unsaturated "styrlyic" alcohols having the structure (III) which may be used are ortho-, meta- and para- derivatives, or mixtures of derivatives of hydroxyl styrene, hydroxyl $\alpha$-methyl styrene, vinyl benzyl alcohol, 2-hydroxyethyl styrene, 2-hydroxypropyl styrene, 2-hydroxypropyl $\alpha$-methyl styrene and 3-hydroxyl-4-methoxyl styrene.

In the more preferred embodiments of this invention the macromer is formed with a head group derived from any desired "styrylic" alcohol and an oligomer which may be (i) a homopolymer of a 1,2-epoxide, or 1,3-epoxide; or (ii) a copolymer of a 1,2-epoxide and/or 1,3-epoxide (OXT) and/or 1,4-epoxide (THF) and/or 1,6-epoxide (OXP); or (iii) a homopolymer of a glycidyl ether (II); or (iv) a copolymer of (II) and a 1,2-, 1,3-, 1,4- or 1,6-epoxide. Random copolymers are formed by simply mixing the monomers, while block copolymers are formed by the sequential addition of the monomers.

The macromer is formed by the action of a cationic ring-opening catalyst identified hereinabove with the "styrylic" alcohol (III) and the alkylene oxide (I) or (II), under mild reaction conditions, namely a temperature in the range from about 0° C. to about 150° C., and more preferably from about 25°-80° C., at ambient or slightly elevated pressure.

The catalyst is used in an amount sufficient to initiate the polymerization. It is most prefered to use a cyclic or acyclic oxonium salt which may be secondary or tertiary. The cyclic oxonium salt may be prepared by reaction of an acyclic oxonium salt with THF. It is most preferred to use a trialkyloxonium or other oxonium salt of the HMF$_6$ acid prepared as described in U.S. Pat. No. 3,585,227. The amount of catalyst used is not critical, from about 0.001 part to about 1 part per 100 parts by wt of oxirane reactants, and more preferably from about 0.01 to about 0.1 part, being generally sufficient. It is desirable, both for economic reasons and for control of the reaction, to keep the amount of catalyst used as low as possible.

The amount of catalyst used has very little effect on the mol wt of the macromer formed, but affects the rate, which in turn affects the temperature of the reaction. Most polymerizations proceed satisfactorily with about 0.05 parts of catalyst per 100 parts of CE. The mol wt is controlled by the ratio of alkylene oxide or glycidyl ether to styrylic alcohol. Because the polymerization proceeds via polyaddition, a designed (desired) mol wt may be obtained. If the mol wt of a macromer is kept relatively low by including from about 2 to about 8 repeating units, the linear macromer is formed substantially free of cyclic oligomers, but at least a trace of cyclic oligomers is always found in practice. Most preferred linear macromers have a Mn in the range from about 200 to about 3000.

A homomacromer of polyepichlorohydrin (PECH) with a styrylic head group is conveniently prepared using hydroxymethyl styrene and ECH and conducting the polymerization reaction in bulk at about 30° C. Infrared, nmr and FD mass spectroscopy, GPC, liquid chromatography (LC), and chemical analyses for chlorine and OH number confirmed the structure of the macromer as being represented by

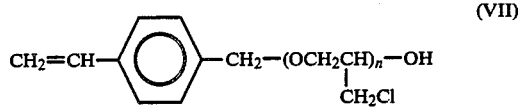

(VII)

wherein n is in the range from 2 to about 100; in an analogous manner other styrylically unsaturated PECH macromers may be prepared having the structure

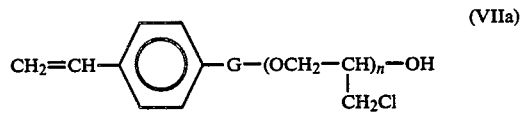

(VIIa)

As is well known, reactive liquid polymers (RLPs) referred to hereinbelow, are used as tougheners for unsaturated polyester resin systems because they cocure with the polyester in addition to contributing to the ease with which it can be handled; the macromers of this invention are used in a manner analogous to that described in U.S. Pat. Nos. Re. 31,469 and Re. 31,468, as tougheners, to provide further options for tailoring the properties of the system.

The styryl-terminated homomacromer (VII) and other macromers having the general structure (IV) are particularly useful as non-aqueous dispersants for sterically stabilized dispersion polymerizations because the terminally unsaturated head group serves to anchor the dispersant by copolymerization with the monomer (for example, acrylic acid) which is to be polymerized. In such polymerizations, shortly after initiation of polymerization, polymer begins to precipitate from the solution and forms aggregates which interfere with the reaction by retarding access of monomer to free radicals. This contributes to poor removal of heat and several related problems. The macromer interferes with formation of the aggregates and the viscosity of the reaction mass is substantially reduced. The effectiveness of the macromer (VII) as a dispersant in a dispersion polymerization of acrylic acid in benzene is illustrated in Example 2 hereinbelow.

Macromers of this invention may be homopolymerized by conventional methods such as by free radical polymerization effected with a lower alkyl peroxide and the like, so as to form a polystyrene polymer with pendant polyether chains; and, they are also used as comonomers in a variety of polymerization reactions with conventional vinyl, acrylic, or diene monomer in which the styryl head group of macromers is copolymerizable.

For example, the macromer (IV), including (V) is copolymerizable with (a) a $C_2$–$C_{12}$ vinyl monomer such as vinyl chloride, vinyl acetate, acrylonitrile, ethylene, propylene, 4-vinylpyridine, vinylpyrrolidone, styrene, 4-chlorostyrene, and the like; (b) a $C_3$–$C_{10}$ monomer such as an unsaturated carboxylic acid or its ester or amide, such as acrylic acid, methacrylic acid, acrylic amide, butyl acrylate, ethyl acrylate, 2-ethylhexyl acrylate, and the like; (c) a $C_4$–$C_{20}$ acyclic or cyclic alkadiene monomer such as butadiene, isoprene, and the like. As a result, a random copolymer of macromer of VIa and VIb is obtained. When the macromer (VII) is copolymerized with ethyl acrylate the random copolymer is represented by the structure

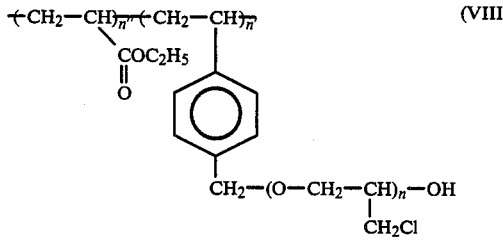

When macromer (VII) is copolymerized with styrene the random copolymer is represented by the structure

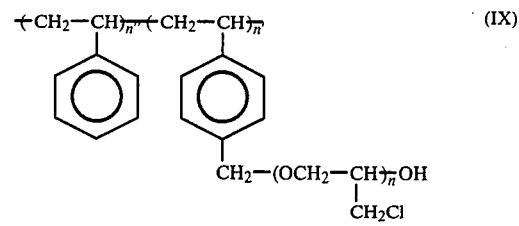

By varying the ratio of conventional vinyl, acrylic, or diene to macromer (VII), and the number of ECH units in the macromer, each of the copolymers may be obtained with a wide range of properties ranging from hard plastic to soft elastomeric.

The macromer is also copolymerizable with reactive liquid polymers (RLPs) such as those having the structure

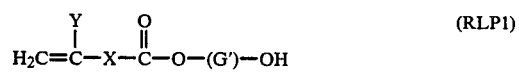

wherein Y is H or alkyl, X is zero, alkylene or arylene, and G' is a polymeric backbone comprising units of at least one epihalohydrin, optionally together with at least one other epoxide; or, the structure

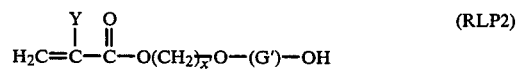

wherein x' is in the range from 2 to 10, and,

Y and G' have the same connotation as that given hereinbove. Preparation of the RLPs is set forth in detail in U.S. Pat. Nos. Re. 31,469 and Re. 31,468 respectively, the disclosures of which are incorporated by reference thereto as if fully set forth herein.

When the macromer (VII) is copolymerized with the RLP1 the copolymer is represented by the structure

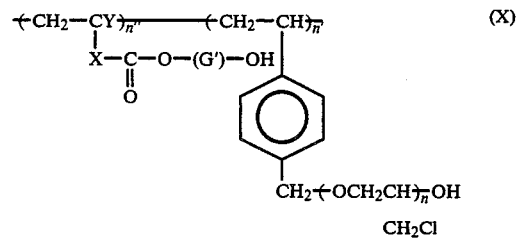

with the backbone terminated conventionally.

In an analogous manner macromer (VII) may be copolymerized with RLP2 to yield a macromer copolymer having the structure

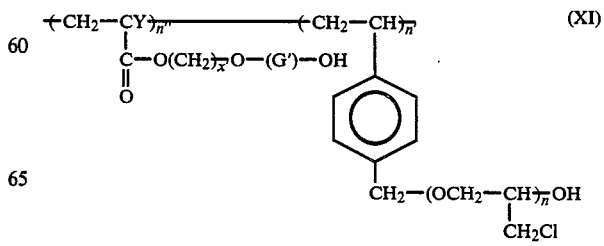

and by varying the ratio of vinyl or acrylic monomer units to the number of PECH units, each of the copolymers may be obtained with a wide range of properties ranging from from hard plastic to soft elastomeric.

Such macromer copolymers are formed by conventional methods, for example, the aforementioned free radical polymerization process. These macromer copolymers with a profusion of pendant OH groups connected to a hydrocarbon backbone, are useful in the production of tailored polyurethanes by reaction with organic isocyanates.

Macromers of this invention may be connected by a diisocyanate to polyether and polyester diols so as to have terminal styrylic groups; many of the resulting polyurethane macromers are conveniently radiation-curable. Quite unexpectedly, the macromer of this invention behaves in a manner analogous to one with an acrylic head group as disclosed in U.S. Pat. Nos. 3,850,770; 3,960,572; 4,367,302; and 4,377,679, pertinent portions of which are incorporated by reference thereto as if fully set forth herein.

After the macromer (VII) is quaternized (aminated), it is particularly useful in the preparation of quaternized oligomers for water treatment and other applications such as antistats and dispersants. Amination of the chloromethyl groups in PECH with a wide variety of aliphatic and aromatic amines is known to produce the corresponding ammonium salt which provides cationic charges and imparts hydrophilicity to the polymer. Thus, the normally hydrophobic PECH oligomer is converted to a hydrophilic polymer, but a polymer with both hydrophilic and hydrophobic characteristics is difficult to obtain. The ability to control these properties allows one to 'fabricate' water-treatment chemicals.

The aminated monomer has the structure

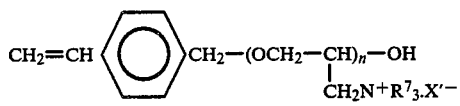
(XII)

wherein

X' represents a halogen, n is an integer in the range from 2 to 100, and $R^7$ represents the residue of an amine used to aminate the macromer.

Because high mol wt quaternized polymers are most preferred for water treatment, and such polymers are aminated only with difficulty, it is particularly convenient to prepare the macromer in a mol wt which is sufficently high to be easily and essentially completely aminated, then homopolymerize or copolymerize the macromer (XII) to produce a polymer with a profusion of substantially fully aminated pendant chains. Such polymers having a Mw in the range from about 100,000 to about 200,000 are effective coagulants, and those in the range from about 500,000 to about 1,000,000 are effective flocculants. It is well known that commercially available Hydrin ® and Herchlor ® PECH elastomers in such desirably high mol wt ranges are aminated with difficulty, and then only to an unsatisfactory extent.

The macromer (VII) in which the OH group is end-capped with an end-capping unit, for example, acrylonitrile, may be block-polymerized with a silyl hydrideterminated polysiloxane to provide an especially effective superwetting agent. The end-capping group is not critical and a variety of esterification and etherification reactions can be used to cap the terminal OH groups, as for example disclosed in U.S. Pat. Nos. 2,998,409 and 3,507,927; British Pat. Nos. 748,856; 848,660; 869,323; 877,256; 911,959; inter alia; or, by reacting with an alkylisocyanate as in British No. 924,259; or, by reacting with diazomethane as in British No. 894,439.

The end-capped macromer is represented by

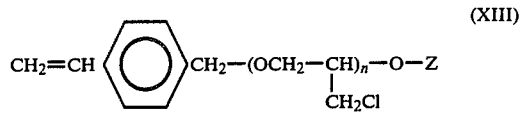
(XIII)

where Z is the residue of the end-capping unit.

In the particular instance when the end-capping unit is an acrylonitrile residue, the structure of the end-capped homomacromer is represented by

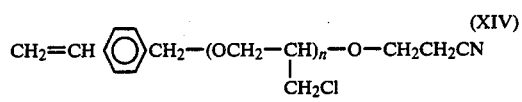
(XIV)

The organohydrosiloxane reactant may be a mono-, di-, or polyhydrosiloxane containing more than two Si-bonded H atoms, wherein any valences of Si not bonded to H or to O in a Si to O to Si bond are bonded to a monovalent hydrocarbon or halaohydrocarbon group, such as those disclosed in greater detail in U.S. Pat. No. 4,150,048 to Schilling et al, the disclosure of which is incorporated by reference thereto as if fully set forth herein. Particularly preferred organohydrosiloxanes have a Si-bonded H at each end as shown by the formula $$HR''_2SiO[R''_2SiO]_zSiR''_2H \qquad (XV)$$

in which R'' is an unsubstituted or halogen-substituted monovalent hydrocarbon group and z is an integer in the range from 0 to about 300, more preferably 5 to 50.

The block copolymer is formed under addition reaction conditions, preferabaly at elevated temperature from about 50°–100° C. in the presence of a non-reactive solvent, and catalyzed by a neutral Pt-containing hydrosilation catalyst such as that described in U.S. Pat. No. 3,220,972, or Pt metal deposited on charcoal, used in concentrations disclosed in U.S. Pat. No. 3,507,815, namely from 0.001 to about 5% by wt of the reactants.

The macromer block copolymer formed may be represented by the formula $$A'A''_2 \qquad (XVI)$$

wherein A' represents the residue of a polysiloxane block (XV) and A'' represents the residue of a polyether block of end-capped macromer (XIV) after it has been aminated.

EXAMPLE 1

In the following illustrative example the macromer (VII) was made by bulk polymerization as described hereinbefore, in a nitrogen atmosphere, with moisture-free reactants charged to a three-necked glass flask, and TEOP catalyst in $CH_2Cl_2$ is dripped into the flask. The flask is equipped with a mechanical agitator, a thermo-probe, and a condenser. One neck was sealed with a rubber septum for the addition of reagents and catalyst solution.

Under N$_2$, sieved epichlorohydrin (25.2 g, 270 mmoles) and vinyl benzyl alcohols (8.0 g, 60 mmoles, a mixture of about 60% meta- and 40% para-) were added into the flask and the solution was brought to 30° C. with a warm water bath. The TEOP was added incrementally with a syringe.

The polymerization is carried out at 28°–36° C. and the temperature is contrtolled by raising or lowering the temperature of the water bath. After 7 hr during which 0.045 g of TEOP was incrementally added, a total solids of 65% was obtained. The polymerization was short-stopped with NH$_4$OH in isopropanol and the product was stabilized with 0.07 g of Irganox 1010 and 0.03 g of MEHQ. The unreacted monomer was removed by rotary evaporation under vacuum at ambient temperature. The product recovered is an easily pourable liquid which is stored at −30° C.

GPC analaysis shows that the macromer has Mn=982 and Mw/Mn=1.8. No high mol wt tail is observed in the GPC curve. This suggests that no significant amount of the macromer is crosslinked prematurely via the styryl head group during the polymerization of ECH. A hydroxyl number of 56 was obtained by titration. It also indicates that the macromer is composed with a single hydroxyl group per polymer chain.

In additional examples a homomacromer (IV) wherein M is a repeating unit of a single CE, was made in an analogous manner by bulk polymerization of each of the following 1,2-epoxides: propylene oxide (PO), n-butyl glycidyl ether (BGE), and dodecylene oxide (DO), respectively. In each case, vinyl benzyl alcohol is used as the unsaturated alcohol which provides the OH group as the propagating species.

In a manner generally analogous to that described hereinabove, a homomacromer of oxetane (Mn=400) is prepared with vinyl benzyl alcohol providing the OH group as the propagating species.

In other examples, a macromer copolymer (IVa) wherein M represents a repeating unit of at least two randomly connected CEs M' and M", is made by bulk polymerization of a mixture of the monomers under conditions analogous to those described hereinabove. Each of the copolymers includes ECH as a comonomer and any one of ethylene oxide (EO), propylene oxide (PO), tetrahydrofuran (THF) and oxepane (OXP); and the copolymers are identified as follows: (EO/ECH); (PO/ECH); (THF/ECH); and, (OXP/ECH).

In a manner analogous to that described hereinabove, the following macromer copolymers are prepared with vinyl benzyl alcohol providing the head group and OH propagating species:
EO/THF; PO/THF; PO/OXP; ECH/BGE; ECH/THF/OXP; and ECH/OXP/BGE.

Homomacromers and macromer copolymers having mol wts (Mn) in the range from about 500-1500, prepared as illustrated in the foregoing examples, are pourable liquids which show characteristic absorption at about 3550 cm$^{-1}$ (broad) assigned to the terminal hydroxyl group and at about 1120 to the C—O stretching of the ether linkage by FT infrared spectroscopic analysis. The C═C stretchings of the vinyl group of the styryl head are overlapped with the stretchings of the aromatic ring. The terminal styryl group of the macromers is also detected by carbon-13 nmr:

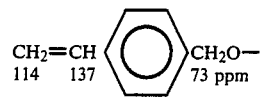

FD mass spectra of these macromers also show a series of species with their molecular weight corresponding to polymers possessing one unit of the vinyl benzyl group and a terminal OH group. For homomacromers, their mol wts correspond to [vinyl benzyl alcohol +(monomer)$_m$] in structure (IV); for macromer copolymers, their mol wts correspond to [vinyl benzyl alcohol +(monomer)$_{m'}$+(monomer)$_{m''}$] corresponding to structure (IV), where m'+m"=m.

In other examples a PECH homomacromer (VII) wherein M is a repeating unit of ECH, is made in a manner analogous to that described hereinbefore with hydroxyl styrene (7.2 g, 60 mmoles). The product recovered is a pourable liquid. FD mass spectra of these macromers also show a series species with their mol wts corresponding to [hydroxyl styrene+(ECH)$_m$] as shown in structure (IV).

It is to be noted that only primary and secondary alcohols provide the desired macromers, and tertiary alcohols are not preferred to produce desirable macromers with a corresponding styryl head.

EXAMPLE 2

PECH homomacromer (VII) as a dispersant in the precipitation polymerization of acrylic acid in benzene To a 1 liter jacketed glass reactor equipped with a reflux condenser and a stirrer, are charged 115 g of acrylic acid, 12 g of (VII) prepared as in Ex. 1 hereinabove, 0.9 g of allyl pentaerythritol as a crosslinking agent, and 620 g of benzene as solvent. The reactor is gradually heated from room temperature while agitating and bubbling nitrogen through the reaction mass. 0.14 g of lauroyl peroxide are added to serve as the free radical initiator when the reaction mass reached 70° C., and the reactor was allowed to reach 80° C. After 4.5 hr the reactor was commenced and it was cooled to room temperature.

The foregoing reaction was repeated under identical conditions except that no homomacromer was added.

The Brookfield viscosity of the reaction mass at 25° C., without the macromer, was 400 cps; for the reaction mass in which the macromer was added the viscosity was 150 cps.

The small homomacromer content of the poly(acrylic acid) does not vitiate the effectiveness of the polymer as a thickener in aqueous solutions. Only 1% by wt of the polymer in water produces a Brookfield viscosity @ 25° C. of 128,000 cps and a pH of 7.6. The polymer produced without the macromer, used at the same 1% by wt, has a viscosity of 129,000 and a pH of 7.5. It is evident that there is no loss in effectiveness of the polymer, but there is a highly desirable improvement in the polymerization conducted as described.

I claim:

1. A process for the manufacture of a polyether macromer having a styryl group near one end and a hydroxyl group at the other, comprising, polymerizing
   (A) a cationically ring-openable cyclic ether selected from the group consisting of
     (i) at least one alkylene oxide having the structure

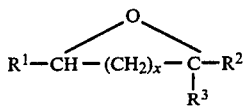 (I)

wherein, x is an integer in the range from 0 to about 4, except that when x>1, a second alkylene oxide having x=1 or 0 must be present, and, $R^1$, $R^2$ and $R^3$ are independently selected from the group consisting of hydrogen, $C_1$-$C_{20}$ alkyl (having from 1 to about 20 carbon atoms) and haloalkyl, and, $C_6$-$C_{20}$ aryl and aralkyl, and, at least one of $R^1$, $R^2$, and $R^3$ is hydrogen; and, (ii) an aliphatic or aromatic glycidyl ether having the structure

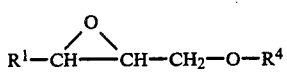 (II)

wherein $R^1$ has the same connotation as hereinabove; and, $R^4$ represents a member selected from the group consisting of $C_1$-$C_{20}$ alkyl or substituted alkyl, haloalkyl, alkoxyalkyl, aryl (Ar), substituted aryl (Ar-Q), wherein Q represents $C_1$-$C_{10}$ alkyl, haloalkyl; and, (B) a monoolefinically ("styrylically") unsaturated primary or secondary alcohol represented by the structure

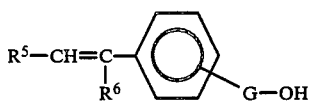 (III)

wherein,

G, if present, is in an ortho-, meta-, or para- position of the phenyl ring which may be substituted, said position being relative to that of the olefinically unsaturated group, and is a spacer selected from the group consisting of branched or linear alkyl, aralkyl, haloalkyl, haloaralkyl, alkoxyl, haloalkoxyl, aralkoxyl and haloaralkoxyl, each having from 1 to about 20 carbon atoms ($C_1$-$C_{20}$); and, $R^5$ and $R^6$ are selected from from the group consisting of hydrogen, $C_1$-$C_{10}$ alkyl (having from 1 to about 20 carbon atoms) and haloalkyl, and, at least one of $R^5$ and $R^6$ is always H;

in the presence of an effective amount of (C) a cationic initiator selected from the group consisting of Friedel-Crafts acids, relatively strong protic organic and inorganic acids, oxonium salts and stable carbenium ions;

so as to produce a macromer having the structure $$R-(M)_m-OH \quad (IV)$$

wherein

R represents the residue of said styrylically unsaturated alcohol,

M represents the residue of at least one said cyclic ether which is ring-opened, and, m represents an integer in the range from 2 to about 500.

2. The process of claim 1 wherein said macromer is selected from the group consisting of a homomacromer of said alkylene oxide (I) selected from the group consisting of a 1,2-epoxide, haloalkyl-1,2-epoxide, and oxetane; and, of said aliphatic and aromatic glycidyl ether (II);

a macromer copolyether copolymer of tetrahydrofuran or oxepane with a comonomer selected from the group consisting of a 1,2-epoxide, a haloalkyl-1,2-epoxide, oxetane, an aliphatic glycidyl ether, and an aromatic glycidyl ether;

a macromer block copolyether represented by the formula $$R-(M')_{m'}-(M'')_{m''}-OH \quad (V)$$

wherein M' and M" represent two ring-opened cyclic ethers, and m' and m" are integers each in the range from 1 to about 300 such that m'+m"=m, of an alkylene oxide (I) selected from the group consisting of a 1,2-epoxide, a haloalkyl-1,2-epoxide, oxetane, an aliphatic glycidyl ether, and an aromatic glycidyl ether; and, a copolymer of macromer having a structure selected from $$[R-(M)_m-OH]_{n'}[M_o]_{n''} \quad (VIa)$$

and, $$[R-(M')_{m'}-(M'')_{m''}-OH]_{n'}[M_o]_{n''} \quad (VIb)$$

wherein, n' represents an integer in the range from 1 to about $10^4$;

n" represents an integer in the range from 1 to about $10^5$;

M' and M" may be present in said macromer as a block copolyether or as a random copolyether copolymer; and, $M_o$ represents an olefinically unsaturated monomer.

3. The process of claim 2 wherein said monoolefinically unsaturated alcohol is selected from the group consisting of a primary alcohol and a secondary alcohol having the structure (III) including ortho-, meta- and para- derivatives of hydroxyl styrene, hydroxyl - methyl styrene, vinyl benzyl styrene, 2-hydroxyethyl styrene, 2-hydroxypropyl styrene, 2-hydroxypropyl - methyl styrene and 3-hydroxyl-4-methoxyl styrene.

4. The process of claim 2 wherein said cationic initiator is selected from the group consisting of boron trifluoride ($BF_3$), boron trifluoride etherate complexes, tin tetrachloride ($SnCl_4$), a fluorinated metallic acid catalyst having the formula $HMF_6$ wherein M is selected from P, As or Sb; an oxonium salt of said acid, and oxonium salts of tetrafluoroboron.

5. The process of claim 4 wherein said monoolefinically unsaturated alcohol is at least partially soluble in the reaction mass subjected to polymerization.

6. The process of claim 5 wherein polymerization is effected in the range from about 0° C. to about 150° C.

7. The process of claim 6 wherein said cationic initiator is present in an amount in the range from 0.001 part to about 1 part by wt per 100 parts by wt of said cyclic ether.

8. The process of claim 7 wherein $M_o$ represents an olefinically unsaturated monomer selected from the group consisting of
   (a) a $C_2$-$C_{12}$ vinyl monomer,
   (b) a $C_3$-$C_{10}$ unsaturated carboxylic acid or its ester, or amide,
   (c) a $C_4$-$C_{20}$ acyclic or cyclic alkadiene.

9. The process of claim 8 wherein
   said vinyl monomer (a) is selected from the group consisting of vinyl chloride, vinyl acetate, acrylonitrile, ethylene, propylene, 4-vinylpyridine, vinylpyrrolidone, styrene, and 4-chlorostyrene;
   said carboxylic acid or carboxylic acid ester or amide (b) is selected from the group consisting of acrylic acid, methacrylic acid, vinyl benzoic acid, vinyl naphthoic acid, acrylic amide, butyl acrylate, ethyl acrylate, 2-hydroxyethyl acrylate, 2-methoxyethyl acrylate, and, 2-ethylhexyl acrylate; and,
   said alkadiene (c) is selected from the group consisting of butadiene, and isoprene.

10. A polyether macromer having a styryl group near one end, a hydroxyl group at the other, and having a molecular weight distribution not exceeding 5.0 and being formed by polymerizing
   (A) a cationically ring-openable cyclic ether selected from the group consisting of
   (i) at least one alkylene oxide having the structure

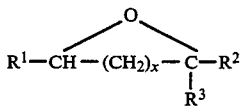  (I)

wherein,
   x is an integer in the range from 0 to about 4, except that when x>1, a second alkylene oxide having x=1 or 0 must be present, and,
   $R^1$, $R^2$ and $R^3$ are independently selected from the group consisting of hydrogen, $C_1$-$C_{20}$ alkyl (having from 1 to about 20 carbon atoms) and haloalkyl, and, $C_6$-$C_{20}$ aryl and aralkyl, and, at least one of $R^1$, $R^2$, and $R^3$ is hydrogen; and,
   (ii) an aliphatic or aromatic glycidyl ether having the structure

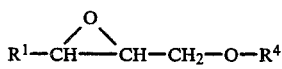  (II)

wherein $R^1$ has the same connotation as hereinabove; and, $R^4$ represents a member selected from the group consisting of $C_1$-$C_{20}$ alkyl or substituted alkyl, haloalkyl, alkenyl substituted alkenyl, haloalkenyl, alkoxyalkyl, aryl (Ar), substituted aryl (Ar—Q), wherein Q is selected from the group consisting of $C_1$-$C_{10}$ alkyl, haloalkyl, $C_2$-$C_{10}$ alkenyl or haloalkenyl; and,
   (B) a monoolefinically ("styrylically") unsaturated primary or secondary alcohol represented by the structure

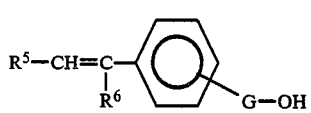  (III)

wherein,
   G, if present, is in an ortho-, meta-, or para- position of the phenyl ring which may be substituted, said position being relative to that of the olefinically unsaturated group, and is a spacer selected from the group consisting of branched or linear alkyl, aralkyl, haloalkyl, haloaralkyl, alkoxyl, haloalkoxyl, aralkoxyl and haloaralkoxyl, each having from 1 to about 20 carbon atoms ($C_1$-$C_{20}$); and,
   $R^5$ and $R^6$ are selected from from the group consisting of hydrogen, $C_1$-$C_{10}$ alkyl (having from 1 to about 20 carbon atoms) and haloalkyl, and, at least one of $R^5$ and $R^6$ is always H;
in the presence of an effective amount of
   (C) a cationic initiator selected from the group consisting of Friedel-Crafts acids, relatively strong protic organic and inorganic acids, oxonium salts and stable carbenium ions;
so as to produce a macromer having the structure $$R\text{—}(M)_m\text{—}OH \qquad (IV)$$

wherein
   R represents the residue of said styrylically unsaturated alcohol,
   M represents the residue of at least one said cyclic ether which is ring-opened, and,
   m represents an integer in the range from 2 to about 500;
whereby said macromer is procuced in conjunction with at least a trace quantity of cyclic oligomer of said cyclic ether.

11. The polyether macromer of claim 10 represented by a homomacromer having the structure

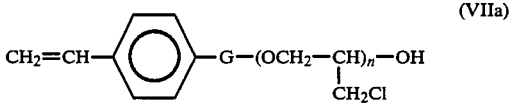  (VIIa)

wherein n is in the range from 2 to about 100.

12. The polyether macromer of claim 10 represented by a macromer copolymer having the structure

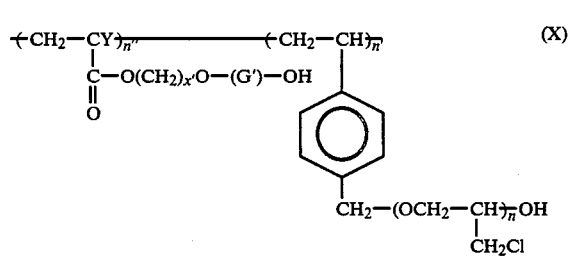  (X)

wherein,
   Y is alkyl or H,
   x' is an integer in the range from 2 to 10,
   G' is a polymeric backbone consisting of plural ether units at least one of which is epichlorohydrin,
   n' represents an integer in the range from 1 to about $10^4$;
   n'' represents an integer in the range from 1 to about $10^5$; and
   the backbone is terminated conventionally.

13. The polyether macromer of claim 10 after it has been aminated so that it is represented by the structure

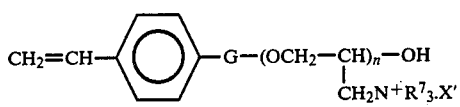

(XII)

wherein
X' represents a halogen,
n is an integer in the range from 2 to 100, and
R$^7$ represents the residue of an amine used to aminate the macromer.

14. A block copolymer of a macromer represented by the formula

A'A"$_2$ wherein
A' represents the residue of a polysiloxane block having the structure HR"$_2$SiO[R"$_2$SiO]$_z$SiR"$_2$H      (XV)

in which R" is an unsubstituted or halogen-substituted monovalent hydrocarbon group and z is an integer in the range from 0 to about 300; and,
A" represents the residue of a macromer having the structure

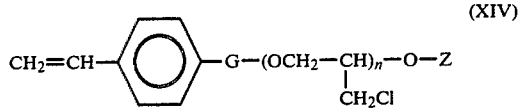

(XIV)

wherein,
G, if present, is in an ortho-, meta-, or para- position of the phenyl ring which may be substituted, said position being relative to that of the olefinically unsaturated group, and is a spacer selected from the group consisting of branched or linear alkyl, aralkyl, haloalkyl, haloaralkyl, alkoxyl, haloalkoxyl, aralkoxyl and haloaralkoxyl, each having from 1 to about 20 carbon atoms ($C_1$–$C_{20}$); n is an integer in the range of from 2 to about 100 and,
Z is the residue of an end-capping unit after it has been aminated.

* * * * *